United States Patent
Gaullier

(12) 
(10) Patent No.: US 6,242,603 B1
(45) Date of Patent: Jun. 5, 2001

(54) PROCESS OF PREPARING LYSERGIC ACID

(75) Inventor: Jean-Claude Gaullier, Gournay sur Marne (FR)

(73) Assignee: Aventis Pharma S.A., Antony Cedex (FR)

( * ) Notice: Subject to any disclaimer, the term of this patent is extended or adjusted under 35 U.S.C. 154(b) by 0 days.

(21) Appl. No.: 09/598,425

(22) Filed: Jun. 21, 2000

Related U.S. Application Data

(60) Provisional application No. 60/161,430, filed on Oct. 26, 1999.

(30) Foreign Application Priority Data

Jul. 2, 1999 (FR) .................................................. 99 08538

(51) Int. Cl.[7] .................................................. C07D 457/02
(52) U.S. Cl. .................................. 546/69; 546/62; 546/67
(58) Field of Search .................................. 546/69, 67, 62

(56) References Cited

PUBLICATIONS

Kobel, H. et al. : 6–Methyl–8–ergolene–8–carboxylic acid, prepared by saprophytic cultivation of appropriate ergot strains in fermenters. Helvetica Chim. Acta, vol. 47, pp. 1052–1064, 1964.*

Oppolzer, W. et al. : Total synthesis of lysergic acid by an intramolecular imino–diels–alder reaction. Helvetica Chim Acta, vol. 64, pp. 478–481, 1981.*

* cited by examiner

*Primary Examiner*—Charanjit S. Aulakh
(74) *Attorney, Agent, or Firm*—Irving Newman

(57) ABSTRACT

The present invention relates to a novel process for preparing lysergic acid by isomerizing paspalic acid, using a tetraalkylammonium hydroxide.

14 Claims, No Drawings

PROCESS OF PREPARING LYSERGIC ACID

CROSS REFERENCE TO RELATED APPLICATIONS

This is a continuation of U.S. patent application Ser. No. 60/161,430, filed Oct. 26, 1999.

The present invention relates to a novel process for preparing lysergic acid by isomerizing paspalic acid.

Lysergic acid is an intermediate in the synthesis of nicergoline, marketed for ameliorating symptoms of failing mental health in the elderly, in retinal problems of vascular origin and in the treatment of acute cerebrovascular accidents.

The synthesis of nicergoline requires the use of a pure lysergic acid, i.e. one which comprises only a small percentage of isolysergic acid.

It is known that lysergic acid can be prepared by isomerizing paspalic acid, using potassium hydroxide (Helvetica Chimica Acta, 64, 47, 478 (1981)) or sodium hydroxide (Helvetica Chimica Acta, 47, 115, 1052 (1964) and JP70013302), but these processes do not allow either good yields or a product comprising small quantities of isolysergic acid to be obtained industrially.

A process has now been found, which is the subject of the present application, allowing lysergic acid of sufficient purity to be obtained in very good yields by isomerizing paspalic acid.

This isomerization is brought about using a tetra($C_1$–$C_6$) alkylammonium hydroxide. It is also possible to use the tetra($C_1$–$C_6$)alkylammonium hydroxide in a mixture with a small quantity of an alkali metal hydroxide.

Tetra($C_1$–$C_6$)alkylammonium hydroxides which may be used are in particular tetramethylammonium hydroxide, tetraethylammonium hydroxide and tetrabutylammonium hydroxide.

Use is preferably made of tetrabutylammonium hydroxide.

The alkali metal hydroxide used may be in particular sodium hydroxide or potassium hydroxide.

Preference is given to the use of sodium hydroxide.

The process is generally carried out in an inert solvent, such as water or an aliphatic ($C_1$–$C_4$) alcohol (methanol or ethanol, for example), or in a mixture of these solvents, at a temperature between 20° C. and 60° C. and preferably between 25 and 35° C. It is advantageous to leave the reaction medium at this temperature for from 20 to 30 hours and in particular for 24 hours.

The quantity of tetra($C_1$–$C_6$)alkylammonium hydroxide is generally from 1.5 to 10 mol and preferably 2.5 mol per mole of paspalic acid.

When use is made of a mixture of tetra ($C_1$–$C_6$) alkylammonium hydroxide and alkali metal hydroxide, the quantity of tetra($C_1$–$C_6$)alkylammonium hydroxide is generally from 0.5 to 2 mol, preferably 1.5 mol, and the quantity of alkali metal hydroxide is generally from 4.5 to 0.5 mol, preferably 1 mol, per mole of paspalic acid.

Still more preferably, the process is carried out in an aqueous medium at a temperature of from 28 to 32° C., either in the presence of 2.5 mol of tetrabutylammonium hydroxide for one mole of paspalic acid or in the presence of 1.5 mol of tetrabutylammonium hydroxide and of 1 mol of sodium hydroxide for one mole of paspalic acid.

The lysergic acid is then precipitated by acidifying the reaction medium, using a mineral acid, preferably using sulphuric acid, and is filtered. It is advantageous to acidify to a pH of about 3–4, in particular to 3.5, while not exceeding 30° C.

The examples below illustrate the invention.

EXAMPLE 1

130 g of paspalic acid are added rapidly to 780.1 g of a 40% strength solution of tetrabutylammonium hydroxide in water, with stirring and under a stream of nitrogen. The mixture is brought to 30±2° C. and allowed to react at this temperature for 20 hours. The reaction medium is cooled to about 20° C. and held at this temperature for 3 h 30 min. 918 g of water are added, followed by acidification using 95% strength sulphuric acid until the pH is 3.5, while maintaining the temperature at about 30° C. The reaction mixture is then cooled to 10±2° C. and held at this temperature for 30 minutes. The mixture is filtered through a sinter funnel under a vacuum of 0.4 bar, washed 3 times with 300 ml of water and then dried for 14 hours at 75±2° C. and 20 mbar. This gives 107 g of lysergic acid comprising less than 3% of isolysergic acid and the RRi is 80% (RRi=weight of 100% lysergic acid isolated/weight of 100% paspalic employed).

EXAMPLE 2

130 g of paspalic acid are added rapidly to 472.3 g of a 40% strength solution of tetrabutylammonium hydroxide in water, with stirring and under a stream of nitrogen, followed by 316 g of a 1.5N aqueous solution of sodium hydroxide. The mixture is brought to 30±2° C. and allowed to react at this temperature for 20 hours. The reaction medium is cooled to about 20° C. and held at this temperature for 3 h 30 min. 918 g of water are added, followed by acidification using 95% strength sulphuric acid until the pH is 3.5, while maintaining the temperature at about 30° C. The reaction mixture is then cooled to 10±2° C. and held at this temperature for 30 minutes. The mixture is filtered through a sinter funnel under a vacuum of 0.4 bar, washed 3 times with 300 ml of water and then dried for 14 hours at 75±2° C. and 20 mbar. This gives 107.8 g of lysergic acid comprising only 2.8% of isolysergic acid and the RRi is 81.6%.

Comparative Tests

A—Preparation of Lysergic Acid with Sodium Hydroxide Alone 5 g of paspalic acid in 100 ml of a 2N aqueous solution of sodium hydroxide are heated at reflux for 2 hours. After cooling, the pH of the reaction medium is brought to 5.5 by adding an aqueous solution of hydrochloric acid and glacial acetic acid (20 ml of water, 10 ml of hydrochloric acid and 10 ml of acetic acid). The precipitate is filtered, washed with 3 times 20 ml of a water/methanol (50:50) mixture, then dried in vacuo at 75° C. This gives 3.15 g of lysergic acid comprising 6.8% of isolysergic acid and the RRi is 59.3%.

B—Preparation of Lysergic Acid with Potassium Hydroxide Alone 5 g of paspalic acid in 360 g of a 0.5N solution of potassium hydroxide in a water/ethanol (50:50) mixture are heated at reflux for 1 hour. After cooling, the pH of the reaction medium is brought to 5.5 by adding 1N hydrochloric acid. The precipitate is filtered, washed with 3 times 20 ml of a water/methanol (50:50) mixture, then dried in vacuo at 75° C. This gives 2.86 g of lysergic acid comprising 1% of isolysergic acid and the RRi is 49.8%.

What is claimed is:

1. A process for preparing lysergic acid by isomerizing paspalic acid, in which the isomerization is brought about using a tetra($C_1$–$C_6$)-alkylammonium hydroxide.

2. A process according to claim 1, in which the tetra($C_1$–$C_6$)alkylammonium hydroxide is selected from tetramethylammonium hydroxide, tetraethylammonium hydroxide and tetrabutylammonium hydroxide.

3. A process according to claim 1 which is carried out in an inert solvent.

4. A process according to claim 3, in which the inert solvent is water or an aliphatic ($C_1$–$C_4$)alcohol or a mixture of these solvents.

5. A process according to claim 1, in which from 1.5 to 10 mol of tetra($C_1$–$C_6$)alkylammonium hydroxide are used for 1 mole of paspalic acid.

6. A process according to claim 5, in which 2.5 mol of tetra($C_1$–$C_6$)-alkylammonium hydroxide are used for 1 mole of paspalic acid.

7. A process according to claim 1, which is carried out at a temperature between 20 and 60° C.

8. A process according to claim 7, which is carried out at a temperature between 25 and 35° C.

9. A process according to claim 1 for preparing lysergic acid by isomerizing paspalic acid, which is carried out using 2.5 mol of tetrabutylammonium hydroxide for 1 mole of paspalic acid in an aqueous medium at a temperature of from 28 to 32° C.

10. A process according to claim 1, which is carried out in the presence of an alkali metal hydroxide.

11. A process according to claim 10, in which the alkali metal hydroxide is chosen from sodium hydroxide and potassium hydroxide.

12. A process according to claim 10, in which from 0.5 to 2 mol of tetra-C1–C6-alkylammonium hydroxide and from 4.5 to 0.5 mol of alkali metal hydroxide are used for 1 mole of paspalic acid.

13. A process according to claim 12, in which 1.5 mol of tetra($C_1$–$C_6$)-alkylammonium hydroxide and 1 mol of alkali metal hydroxide are used for 1 mole of paspalic acid.

14. A process for preparing lysergic acid by isomerizing paspalic acid, which is carried out using 1.5 mol of tetrabutylammonium hydroxide and 1 mol of sodium hydroxide for 1 mole of paspalic acid in an aqueous medium at a temperature of from 28 to 32° C.

\* \* \* \* \*